(12) United States Patent
Ketelson et al.

(10) Patent No.: US 8,318,144 B2
(45) Date of Patent: Nov. 27, 2012

(54) USE OF PEO-PBO BLOCK COPOLYMERS IN OPHTHALMIC COMPOSITIONS

(75) Inventors: Howard Allen Ketelson, Dallas, TX (US); Nathaniel D. McQueen, Vienna, VA (US)

(73) Assignee: Alcon Research, Ltd., Fort Worth, TX (US)

( * ) Notice: Subject to any disclaimer, the term of this patent is extended or adjusted under 35 U.S.C. 154(b) by 525 days.

(21) Appl. No.: 11/953,654

(22) Filed: Dec. 10, 2007

(65) Prior Publication Data
US 2008/0138310 A1 Jun. 12, 2008

Related U.S. Application Data

(60) Provisional application No. 60/869,513, filed on Dec. 11, 2006.

(51) Int. Cl.
*A61K 31/74* (2006.01)
*A61K 31/13* (2006.01)

(52) U.S. Cl. ..................... 424/78.04; 514/668

(58) Field of Classification Search ............... 514/668; 424/78.04
See application file for complete search history.

(56) References Cited

U.S. PATENT DOCUMENTS

| | | | |
|---|---|---|---|
| 2,174,761 | A | 10/1939 | Schuette et al. |
| 2,674,619 | A | 4/1954 | Lundsted |
| 2,828,345 | A | 3/1958 | Spriggs |
| 3,050,511 | A | 8/1962 | Szwarc |
| 3,829,506 | A | 8/1974 | Schmolka et al. |
| 4,057,598 | A | 11/1977 | Lundberg et al. |
| 4,104,824 | A | 8/1978 | Lundberg et al. |
| 4,130,517 | A | 12/1978 | Lundberg et al. |
| 4,326,977 | A * | 4/1982 | Schmolka ............ 510/132 |
| 4,360,451 | A | 11/1982 | Schmolka |
| 4,504,405 | A * | 3/1985 | Howes ............ 134/26 |
| 5,037,647 | A | 8/1991 | Chowhan et al. |
| 5,075,400 | A | 12/1991 | Andrade et al. |
| 5,277,911 | A | 1/1994 | Viegas et al. |
| 5,342,620 | A | 8/1994 | Chowhan |
| 5,370,744 | A | 12/1994 | Chowhan et al. |
| 5,376,693 | A * | 12/1994 | Viegas et al. ............ 523/106 |
| 5,480,633 | A | 1/1996 | Simion et al. |
| 5,505,953 | A | 4/1996 | Chowhan |
| 5,631,005 | A | 5/1997 | Dassanayake et al. |
| 5,756,443 | A | 5/1998 | Inoue et al. |
| 5,773,396 | A | 6/1998 | Zhang et al. |
| 5,811,466 | A | 9/1998 | Chowhan et al. |
| 5,981,255 | A | 11/1999 | Miyota et al. |
| 6,004,923 | A | 12/1999 | Oftring et al. |
| 6,057,283 | A | 5/2000 | Oftring et al. |
| 6,143,799 | A | 11/2000 | Chowhan et al. |
| 6,204,238 | B1 | 3/2001 | Oftring et al. |
| 6,214,596 | B1 * | 4/2001 | Asgharian et al. ............ 435/188 |
| 6,319,464 | B1 | 11/2001 | Asgharian |
| 6,320,064 | B1 | 11/2001 | Oftring et al. |
| 6,365,636 | B1 | 4/2002 | Chowhan et al. |
| 6,503,497 | B2 | 1/2003 | Chowhan et al. |
| 6,656,504 | B1 | 12/2003 | Bosch et al. |
| 6,664,294 | B1 | 12/2003 | Park et al. |
| 6,849,253 | B2 | 2/2005 | Chowhan et al. |
| 7,282,178 | B2 | 10/2007 | Salamone et al. |
| 2002/0064514 | A1 | 5/2002 | Viegas et al. |
| 2002/0141899 | A1 | 10/2002 | Tsao |
| 2004/0052746 | A1 | 3/2004 | Tamareselvy et al. |
| 2004/0241130 | A1 | 12/2004 | Tamareselvy et al. |
| 2005/0250661 | A1 | 11/2005 | Bragulla |

FOREIGN PATENT DOCUMENTS

| | | |
|---|---|---|
| GB | 722746 | 1/1955 |
| WO | 03043668 | 5/2003 |

OTHER PUBLICATIONS

Nace, Contrasts in the Surface Activity of Polyoxypropylene and Polyoxybutylene-based Block Copolymer Surfactants; JAOCS, vol. 73, No. 1, (1996) pp. 1-9.

Yu, et al., Association of Diblock and Triblock Copolymers of Ethylene Oxide and Butylene Oxide in Aqueous Solution, Langmuir, vol. 12, (1996) pp. 3404-3412.

Yang, et al. Effect of Block Structure on the Micellization and Gelation of Aqueous Solutions of Copolymers of Ethylene Oxideand Butylene Oxide; Macromolecules; vol. 27; (1994); pp. 2371-2379.

Ketelson, et al.; Dynamic Wettability Properties of a Soft Contact Lens Hydrogel; Colloids and Surfaces B: Biointerfaces; vol. 40; (2005); pp. 1-9.

Bedells, et al.; Micellisation of Diblock Copoly(oxyethylene/oxybutylene) in Aqueous Solution; J. Chem. Soc. Faraday Trans; vol. 89; No. 8; (1993); pp. 1235-1242.

Yang, et al.; Micellization of Diblock and Triblock Copolymers in Aqueous Solution. New Results for Oxyethylene/Oxybutylene Copolymers E38B12 and E21B11E21. Comparison of Oxyethylene/Oxybutylene, Oxyethylene/Oxpropylene, and Oxyethylene/Alkyl Systems; Langmuir; vol. 11; (1995); pp. 4708-4711.

Kelarakis, et al.; Temperature Dependencies of the Critical Micelle Concentrations of Diblock Oxyethylene/Oxybutylene Copolymers. A Case of Athermal Micellization; Macromolecules; vol. 31; (1998); pp. 944-946.

Chaibundit, et al.; Association Properties of Triblock Copolymers in Aqueous Solution: Copolymers of Ethylene Oxide and 1,2-Butylene Oxide with Long E-blocks; Langmuir; vol. 16; (2000); pp. 9645-9652.

* cited by examiner

*Primary Examiner* — Benjamin Packard
*Assistant Examiner* — Adam Milligan
(74) *Attorney, Agent, or Firm* — Gregg C. Brown; Michael D. Rein

(57) ABSTRACT

The use of poly(oxyethylene)-poly(oxybutylene) block copolymers in pharmaceutical compositions useful for modifying the surfaces of contact lenses and other medical devices is disclosed. The present invention is based in-part on a discovery that this class of compounds is particularly efficient in wetting hydrophobic surfaces, such as the surfaces of silicone hydrogel contact lenses and other types of ophthalmic lenses. Such compounds are also useful for cleaning purposes. The use of the compounds as surfactants in various types of compositions for treating contact lenses therefore represents a preferred embodiment of the present invention.

17 Claims, No Drawings

USE OF PEO-PBO BLOCK COPOLYMERS IN OPHTHALMIC COMPOSITIONS

This application claims priority from U.S. Provisional Application Ser. No. 60/869,513, filed on Dec. 11, 2006.

FIELD OF THE INVENTION

The present invention is directed to ophthalmic compositions containing one or more block copolymers referred to as (polyoxyethylene)-(polyoxybutylene) block copolymers ("PEO-PBO"). The invention is particularly directed to the use of PEO-PBO block copolymers as wetting and/or cleaning agents in compositions for treating contact lenses.

BACKGROUND OF THE INVENTION

Hydrogels are water swollen three-dimensional polymeric networks that are used in a variety of biomedical applications including drug delivery agents, prosthetic devices and contact lenses. It is well established that the surface characteristics of hydrogels are determined by the orientation of hydrophobic and hydrophilic moieties of the macromolecules. See, e.g., Ketelson et al., Colloids and Surfaces B: Biointerfaces, Vol. 40, pages 1-9 (2005).

Because contact lenses are in intimate contact with the corneal surface and the human tear film, which is composed of proteins, lipids, inorganic cations (e.g., calcium) and mucins, the biocompatibility characteristics of the lenses are directly affected by the surface wettability properties of the hydrogel materials, from which the lenses are formed. In particular, evaluating the surface wettability properties of a lens material is important because such properties affect the stability of the tear film. To maintain a stable tear film, a contact lens material must have hydrophilic surface properties. If the contact lens material becomes hydrophobic, the tear film may be disrupted. To determine the wettability of a surface via an aqueous solution, such as human lacrimal fluid, i.e., tears, the contact angle is measured. The spreading of an aqueous fluid on a surface indicates that the surface is hydrophilic, thereby resulting in a low contact angle. The surface is hydrophobic if a drop of aqueous fluid does not spread, thereby resulting in a high contact angle.

A new family of contact lens materials, silicone hydrogels ("SiH"), is gradually replacing traditional hydrogels as the material of choice for extended wear soft contact lenses. Silicone hydrogel materials have significantly higher oxygen permeability than traditional soft lens hydrogels due to the presence of siloxane functional groups. Additionally, the presence of siloxane groups in SiH materials results in a lens surface having hydrophobic properties. An example of a SiH lens is the Acuvue Advance® contact lenses marketed by Johnson & Johnson.

Various techniques, for example, plasma surface treatments and incorporation of molecules within the lens material, have been utilized in order to provide a biocompatible, hydrophilic and wettable lens surface. Although modifying the surface can improve biocompatibility, it has also been reported that some silicone hydrogel materials accumulate lipids over time, and that this build-up may result in a decrease in the wettability of the silicone hydrogel lens material and surface.

The wettability characteristics of the surfaces of contact lenses may also be modified by reducing the amount of hydrophobization on the surfaces. Surfactants have been utilized in prior compositions for treating contact lenses, for example poloxamers and poloxamines, such as the Pluronic® and Tetronic® brands of surfactants, which are poly(oxyethylene)-poly(oxypropylene) ("PEO-PPO") block copolymers, have been used extensively in prior products utilized to treat contact lenses. However, such surfactants do not wet SiH lenses efficiently.

British Patent No. 722,746 (Lundsted) discloses surface active compounds derived from higher α, β alkylene oxides.

U.S. Pat. No. 2,828,345 (Spriggs) discloses hydroxypolyethylene diethers of polyoxybutylene glycols.

U.S. Pat. No. 4,360,451 (Schmolka) discloses amphoteric surfactant gels containing a polyoxybutylene-polyoxyethylene block copolymer.

In view of the foregoing, there is a need for new methods and compositions for modifying silicone hydrogel lens materials to impart improved surface wetting and biocompatibility characteristics during wear. The present invention is directed to satisfying this need.

SUMMARY OF THE INVENTION

The present invention is directed to the use of block copolymers referred to as (polyoxyethylene)-(polyoxybutylene) block copolymers ("PEO-PBO") to modify the surface properties of ophthalmic medical devices, so as to enhance the wettability of the devices, and facilitate cleaning of the devices. The PEO-PBO block copolymers described herein may be contained in various types of compositions for treating medical devices, such as wetting solutions, soaking solutions, cleaning and comfort solutions, and disinfection solutions. The present invention is particularly directed to the use of PEO-PBO copolymers in such compositions for treating contact lenses, especially SiH lenses.

The primary function of the PEO-PBO block copolymers in the compositions of the present invention is to treat the surface of a medical device, particularly an ophthalmic device, such as a contact lens or an intraocular lens. Such treatment facilitates the wettability of the device and/or the cleaning of the device. This surface treatment has been found to be particularly effective relative to enhancing the wettability of SiH contact lenses.

The block copolymers may also be utilized to: (a) enhance the antimicrobial activity of ophthalmic compositions; (b) prevent or reduce the uptake of biocides by contact lenses; (c) stabilize tear films; (d) facilitate the removal of proteins and/or lipids from the surfaces of contact lenses; (e) prevent protein and lipid deposit formation; (f) stabilize ocular emulsions; (g) prevent or reduce uptake of biocides or drugs into contact lenses or onto container surfaces; (h) function as a drug solubilizer; (i) enhance drug penetration; (j) function as comfort and cushioning agents; and/or (k) decrease the adhesion of microbes to the surfaces of contact lenses or other medical devices. All of the above utilities for the block copolymers of the present invention depend on the block chemistry being used, i.e, the ratio of hydrophilic (PEO) to hydrophobic (PBO) segments. The copolymers are effective at low concentrations, may be instilled directly into the eye, and are compatible with antimicrobial agents utilized to preserve aqueous pharmaceutical compositions from microbial contamination and/or to disinfect contact lenses.

The present invention is based in-part on a finding that PEO-PBO block copolymers can be used to effectively modify contact lens surface properties at low concentrations. More specifically, it has been discovered that the PEO-PBO block copolymers described herein are retained on hydrophobic surfaces effectively and efficiently, thereby changing the wettability of the surfaces, as reflected in improved and superior wetting properties.

Although there may be several reasons for this change in surface chemistry using the PEO-PBO block copolymers, it is believed that by using poly(oxybutylene) as the hydrophobic block, the surface active properties are significantly different from those of surfactants currently used in lens care products, such as poloxamers and poloxamines. It has been shown that PEO-PBO block copolymers, relative to known PEO-PPO block copolymers, such as Pluronic® and/or Tetronic® block copolymers, display superiority in reducing surface tension at interfaces, pack more efficiently at interfaces, have lower critical micelle concentrations and can be produced with high purity (low polydispersity). By using a more hydrophobic block, i.e., oxy(butylene) versus oxy(propylene), a lower molecular weight block copolymer can be prepared with significant hydrophobic character. The hydrophobic character of the oxybutylene provides improved interfacial properties. These properties lead to high rates of diffusion to an interface or substrate and greater retention/improved substantivity on hydrophobic surfaces, and allow lower concentrations to be used to achieve a desired property, compared to the concentrations required for PEO-PPO block copolymers such as the Pluronic® and Tetronic® brands of surfactants that have been extensively used in prior compositions for treating contact lenses. The above-described characteristics of the PEO-PBO block copolymers offer significant advantages over other known block copolymers.

A first embodiment of the present invention is directed to a method of modifying the surface of a contact lens which comprises placing the lens in an amount of a contact lens treatment solution of the type described herein sufficient to cover the lens, and soaking the lens in the solution. Another embodiment is directed to a method of wetting a contact lens with said aqueous solution and to a silicone hydrogel contact lens wherein a poly(oxyethylene)-poly(oxybutylene) block copolymer is absorbed within the lens matrix and/or adsorbed to surfaces of the lens.

Another embodiment is directed to ophthalmic compositions comprising at least one poly(oxyethylene)-poly(oxybutylene) block copolymer of the type described herein and an ophthalmically acceptable vehicle therefor. Such compositions may be formulated so as to achieve wetting of contact lenses, cleaning of contact lenses, or both wetting and cleaning of contact lenses.

The present invention is more fully discussed with the aid of the following figures and detailed description below.

The present invention will be better appreciated by reference to the following Detailed Description.

DETAILED DESCRIPTION OF INVENTION

As utilized herein, the following abbreviations and terms, unless otherwise indicated, shall be understood to have the following meanings:

The abbreviation "SiH" means silicone hydrogel.

The abbreviation "PEO-PPO" means poly(oxyethylene)-poly(oxypropylene).

The abbreviation "PEO-PBO" means poly(oxyethylene)-poly(oxybutylene).

The abbreviation "PEO-PBO-PEO" means poly(oxyethylene)-poly(oxybutylene)-poly(oxyethylene).

The abbreviation "PEG" means polyethylene glycol.

The abbreviation "b.d.l." means below detection limit.

The abbreviation "PHMB" means polyhexamethylene biguanide.

The abbreviation "mOsm/kg" means milliosmoles/kilogram of water.

The abbreviation "pHEMA" means poly(2-hydroxyethyl methacrylate).

The abbreviation "HLB" means hydrophilic-lipophilic balance.

The abbreviation "EO" means oxyethylene.

The abbreviation "BO" means oxybutylene.

The term "contact angle" is a quantitative measure of the wetting of a solid by a liquid and defined geometrically as the angle formed by a liquid where liquid, gas and solid phases intersect. Alternative, related terms that may be used herein include "wetting angle" or "advancing contact angle."

The term "hydrophilic" means having a strong affinity for water. Alternative, related terms that may be used herein include "hydrophilicity".

The term "hydrophobic" means having little or no affinity for water. Alternative, related terms that may be used herein include, "hydrophobicity".

The term "pHEMA-MAA" means contact lenses comprised of poly(2-hydroxyethyl methacrylate-co-methacrylic acid). Exemplary pHEMA-MAA lenses include "Acuvue® 2" (Johnson & Johnson).

The term "surfactant" means a substance capable of reducing the surface tension of a liquid, e.g., water or an aqueous solution, in which the substance is dissolved.

The term "wetting" means converting a hydrophobic surface whereon a liquid (e.g., water) does not spread because the liquid has an increased surface tension to a surface that is hydrophilic whereon the liquid spreads readily because its surface tension is reduced, as determined by a contact angle experiment. Alternative, related terms that may be used herein include "wettability".

The term "uptake" refers to the amount of surfactant that is absorbed and/or adsorbed by a contact lens or other medical device. Alternative terms that may be used herein include, "uptake concentration", "surfactant uptake", "uptake results", "uptake data" and "uptake concentration of surfactants".

The term "oxyethylene" means a two carbon alkylenyl group bonded to an oxygen atom, for example —$CH_2$—$CH_2O$—.

The term "oxybutylene" means a four carbon alkenyl group bonded to an oxygen atom, for example, —[$OCH_2C(CH_2CH_3)H$]—.

The term "block copolymer" is a polymer that has at least one homopolymeric chain of one monomer and at least one additional homopolymeric chain of a second monomer. Exemplary configurations of such block copolymers include branched, star, di-block, tri-block and cyclic, wherein the cyclic configuration is preferred.

The term "homopolymer" means a polymer formed from a single monomer; for example, polyethylene formed by polymerization of ethylene.

The term "an amount effective to preserve" means an amount of an antimicrobial agent effective in producing the desired effect of preserving the solutions described herein from microbial contamination, preferably an amount which, either singly or in combination with one or more additional antimicrobial agents, is sufficient to satisfy the preservative efficacy requirements of the United States Pharmacopoeia ("USP").

The term "an amount effective to disinfect" means an amount of antimicrobial agent effective in producing the desired effect of disinfecting contact lenses by substantially reducing the number of viable microorganisms present on the lenses, preferably an amount which, either singly or in combination with one or more additional antimicrobial agents, is sufficient.

The term "an amount effective to clean" means an amount of a cleaning agent that facilitates removing, and is preferably effective to remove, debris or deposit material from a contact lens contacted with the cleaning agent containing composition.

The term "ophthalmically acceptable vehicle" means a pharmaceutical composition having physical properties (e.g., pH and/or osmolality) that are physiologically compatible with ophthalmic tissues.

The block copolymers utilized in the present invention comprise compounds that contain hydrophilic and hydrophobic segments that can be altered to control the HLB (hydrophilic-lipophilic balance), molecular weight and other properties of the block copolymers using well known anionic polymerization techniques. More particularly, the block copolymers of the present invention are those that include a poly(oxyethylene) block as the hydrophilic component and a poly(oxybutylene) block as the hydrophobic component. These may be in form of a di-block copolymer, denoted as PEO-PBO, a tri-block copolymer, represented as PEO-PBO-PEO or PBO-PEO-PBO, or other block-type configurations. Unless expressly indicated to the contrary, all references to "PEO-PBO block copolymers" herein include all of the foregoing forms. These copolymers may also be described in terms of the approximate or average value assigned to the respective repeating group. For example, $(EO)_{20}(BO)_5$, where the average value of the oxyethylene group is 20, and the average value of the oxybutylene group is 5.

Preferred polymers of the present invention are di-block copolymers of the following general formula:

$$(EO)_m(BO)_n \qquad (I)$$

wherein m is an integer having an average value of 10 to 1000 and n is an integer having an average value of 5 to 1000.

PEO-PBO di-block copolymers of the following general formula are particularly preferred:

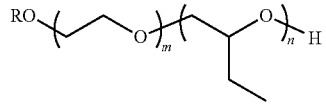

(II)

wherein R is selected from the group consisting of hydrogen, methyl, ethyl, propyl and butyl; m is an integer having an average value of 10 to 1000; and n is an integer having an average value of 5 to 1000.

Most preferred is a copolymer of formula (II) wherein R is methyl; m has an average value of 45; and n has an average value of 10.

The PEO-PBO block copolymers utilized in the present invention have a molecular weight in the range of 1,000 to about 100,000 Daltons; and more preferably in the range of 1,000 to about 15,000 Daltons.

Maintaining a proper hydrophilic-lipophilic balance (HLB) imparts certain properties to the PEO-PBO block co-polymer compositions of the present invention. For example, the HLB of the block co-polymers utilized in the compositions of the present invention is directly related to the solubility, surface wettability, and interfacial surface activity properties of the compositions of the present invention.

The BO portion of the block copolymer of formula (I) is hydrophobic and is primarily responsible for the wettability properties of the compositions described herein. The EO portion of the copolymer provides the compositions with hydrophilic properties, but more importantly, it is this portion of the co-polymer that determines the aqueous solubility of the copolymers. Although it is possible to utilize solubilizing agents in the compositions of the present invention, in which case the ratio of the EO to BO segments is somewhat less critical, it is preferred to utilize copolymers that do not require solubilizing agents, as such compounds may disrupt or modify the HLB, which in turn may adversely affect the wettability properties of the compositions, cause ocular irritation, or create other concerns. Therefore, the preferred copolymers of formula (I) are those wherein there is a predominance of EO to BO segments. That is, the variable "m" in formula (I) and formula (II) above is preferably greater than the variable "n". The PEO-PBO block co-polymers will preferably have a ratio of EO to BO segments of from about 2:1 to about 10:1, with a ratio of about 3:1 to about 6:1 being most preferred.

The foregoing PEO-PBO block copolymers may be prepared by the application or adaptation of known methods described in the literature, for example, as described in Nace, V. M. *J. Am. Oil Chem. Soc.* 1996, 73, 1; Yang, Z.; Pickard, S.; Deng, N.-J.; Barlow, R. J.; Attwood, D.; Booth, C. *Macromolecules* 1994, 27, 2371; Yang, Y.-W.; Deng, N.-J.; Yu, G.-E.; Zhou, Z.-K.; Attwood, D.; Booth, C. *Langmuir* 1995, 11, 4703; Yu, G.-E.; Yang, Y.-W.; Yang, Z.; Attwood, D.; Booth, C.; Nace, V. M. *Langmuir* 1996, 12, 3404; Chaibundit, C.; Mai, S.-M.; Heatley, F.; Booth, C. *Langmuir* 2000, 16, 9645; Bedells, A. D.; Arafeh, R. M.; Yang, Z.; Attwood, D.; Heatley, F.; Pedget, J. C.; Price, C.; Booth, C. *J. Chem. Soc. Faraday Trans.* 1993, 89, 1235; and Kelarakis, A.; Havredaki, V.; Yu, G.-E.; Derici, L.; Booth, C. *Macromolecules* 1998, 31, 944, the entire contents of each of which are hereby incorporated in the present specification by reference. The foregoing PEO-PBO block copolymers may also be prepared by the application or adaptation of known methods described in U.S. Pat. Nos. 2,828,345 (Spriggs), and 2,174,761 (Schuette et al.), the entire contents of each of which are hereby incorporated into the present specification by reference.

The PEO-PBO block copolymers described above may be synthesized using a well defined polyethylene glycol (PEG) polymer by controlled addition of oxybutylene to the primary hydroxyl group of the PEG polymer. For example, the PEO-PBO di-block copolymer $(EO)_{45}(BO)_{10}$ may be prepared according to the following general reaction scheme:

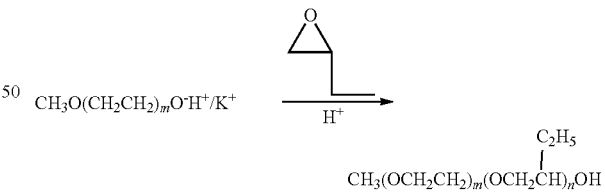

Other variations of the block chemistry structure may also be prepared, using techniques and methods readily available and well-known to those skilled in art. For example, the following reaction process may be utilized for the preparation of tri-block copolymers of the form $(EO)_m(BO)_n(EO)_m$:

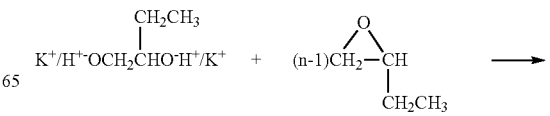

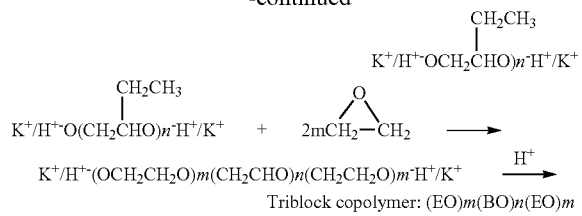

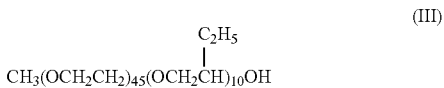

The above-described block copolymers and variations thereof may be used in combination, either with each other, or with other types of polymers. For example, PEO-PBO block copolymers or variations thereof may be used in combination with nonionic surfactants (e.g., poloxamer and poloxamine block copolymers, such as the Tetronic® brand of surfactants available from BASF) to provide additive or synergistic effects where appropriate. In a preferred embodiment, the PEO-PBO block polymers of the present invention are used in combination with poloxamine block copolymers. The PEO-PBO block copolymers may also be functionalized with specific end groups for specific surface reactions to covalently bind the polymer to a surface or prepare a new polymer material. The PEO-PBO block copolymers that may be utilized in the present invention are not limited relative to structure or molecular weight, so long as the block copolymers are soluble in aqueous solutions and are non-toxic to ophthalmic tissue at concentrations on the order of those described herein.

The amount of PEO-PBO block copolymer required in the compositions of the present invention will vary depending on the particular block copolymer selected and the purpose or function for which the block copolymer is being utilized (e.g., contact lens cleaning, contact lens wetting and/or inhibition of uptake of lipids or other biomolecules), as well as on other variables, such as the identity and physical properties of other components in the compositions. The determination of the ideal concentration of a particular copolymer in a given composition can be determined through routine testing. Such concentrations are referred to herein by means of the function to be performed by the PEO-PBO block copolymers, such as, "an amount effective to clean", "an amount effective to enhance wettability", "an amount effective to inhibit the uptake of biomolecules", and so on.

The total amount of PEO-PBO block copolymers contained in the compositions of the present invention will typically be in the range of 0.001 to about 1 weight/volume percent ("w/v %"), preferably about 0.05 to 0.5 w/v %, and more preferably between 0.1 to 0.2 w/v %.

The block copolymers of the present invention may also be combined with other components commonly utilized in products for treating contact lenses, such as rheology modifiers, enzymes, antimicrobial agents, surfactants, chelating agents, buffering agents or combinations thereof.

The compositions may also contain one or more poly(oxyethylene)-poly(oxypropylene) block copolymers such as poloxamer or poloxamine copolymers (e.g., poloxamine 1304, which is commercially available as "Tetronic® 1304"). Poloxamers, also known by the trade name Pluronic™, are nonionic block copolymers composed of a central hydrophobic chain of poly(oxypropylene) flanked by two hydrophilic chains of poly(oxyethylene). Poloxamines, also known by the trade name Tetronic™, are tetrafunctional block copolymers which contain four polyethylene oxide (PEO)-polypropylene oxide (PPO) chains joined to the nitrogen atoms of a central ethylene diamine moiety. A particularly preferred embodiment of the present invention is a composition comprising a block copolymer of the formula $$CH_3(OCH_2CH_2)_{45}(OCH_2CH)_{10}OH \quad (III)$$
(with $C_2H_5$ branch)

and poloxamine 1304.

One or more of the above-described poly(oxyethylene)-poly(oxypropylene) block copolymers may be contained in the compositions of the present invention in an amount effective to facilitate wetting and/or cleaning of contact lenses, which is referred to herein as an "effective amount". Such amount will typically be in the range of 0.001 to about 1 weight/volume percent ("w/v %"), preferably about 0.05 to 0.5 w/v %, and more preferably between 0.1 to 0.2 w/v %.

The compositions of the present invention may contain one or more ophthalmically acceptable antimicrobial agents in an amount effective to preserve the solution from microbial contamination of the solutions or in an amount effective to disinfect contact lenses by substantially reducing the number of viable microorganisms present on the lenses. The levels of antimicrobial activity required to preserve ophthalmic compositions from microbial contamination or to disinfect contact lenses are well known to those skilled in the art, based both on personal experience and official, published standards, such as those set forth in the United States Pharmacopoeia ("USP") relative to preservative efficacy, and EN ISO 14729: 2001 relative to contact lens disinfection, and similar publications.

The invention is not limited relative to the types of antimicrobial agents that may be utilized. The preferred biocides include: alkyl amidoamines, polyhexamethylene biguanide polymers ("PHMB"), polyquaternium-1, and amino biguanides, such as those described U.S. Pat. No. 6,664,294. The most preferred antimicrobial systems are polyquaternium-1 and a combination of polyquaternium-1 and myristamidopropyl dimethylamine ("MAPDA").

Amidoamines and amino alcohols may also be utilized to enhance the antimicrobial activity of the compositions described herein. The preferred amidoamines are MAPDA and related compounds described in U.S. Pat. No. 5,631,005 (Dassanayake, et al). The preferred amino alcohols are 2-amino-2-methyl-1-propanol ("AMP") and other amino alcohols described in U.S. Pat. No. 6,319,464. The entire contents of the '005 and '464 patents are hereby incorporated in the present specification by reference.

The compositions of the present invention that are adapted for the treatment of contact lenses may include agents to enhance the cleaning or disinfection of the lenses. Such agents may include polycarboxylates, for example, citrate, as described in U.S. Pat. Nos. 5,370,744 and 5,037,647, the entire contents of each of which are hereby incorporated in the present specification by reference.

The compositions must be sterile, aqueous, and physiologically compatible. The compositions will typically have a pH in the range of 6.0 to about 9.0, and preferably in the range of 6.5 to 8.0. Although sodium hydroxide can be used to increase the pH of the formulations, other bases such as triethanolamine, 2-amino-butanol, 2-amino-2-methyl-1-propanol (AMP) and tris(hydroxymethyl) aminomethane may also be used.

A variety of buffering agents may be utilized in the compositions of the present invention, such as sodium borate, boric acid, sodium citrate, citric acid, sodium bicarbonate, phosphate buffers and combinations thereof. Borate and polyol systems may also be used to provide buffering, to enhance antimicrobial activity, or to provide both buffering and an enhancement of antimicrobial activity, or other useful properties to the compositions of the invention. The borate and polyol systems which may be used include those described in U.S. Pat. Nos. 6,849,253; 6,503,497; 6365,636; 6,143,799; 5,811,466; 5,505,953; and 5,342,620; the entire contents of each are hereby incorporated in the present specification by reference.

The ophthalmic compositions of the present invention will generally be formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

The above-described compositions may be used to treat contact lenses or other devices in accordance with processes known to those skilled in the art. More specifically, the lenses will first be removed from the eyes of the patients, and then will be immersed in the compositions of the present invention for a time sufficient to achieve the desired effect, e.g., increased wettability, cleaning and/or prevention of biocide uptake. This immersion will typically be accomplished by means of soaking the lenses in a solution for a period ranging from a few hours (e.g, approximately two to four hours) to overnight (e.g., approximately six to eight hours). The lenses will then be rinsed and placed in the eye. Prior to immersion in the said compositions, the lenses will preferably also be rinsed to facilitate cleaning. However, the compositions of the present invention may also be formulated as wetting drops that are applied directly to contact lenses while being worn by human patients. The compositions may also be utilized as packaging solutions for contact lenses, i.e., solutions in which the contact lenses are stored from the time of manufacture until a sale to a contact lens wearer.

The present invention may be better understood by reference to the following examples, which are provided to further illustrate certain preferred embodiments of the invention, and should in no way be construed as limiting the scope of the invention. In the following Example, various methods known to one skilled in the art may be employed to measure the contact angle for lenses according to the present invention. Exemplary methods include, but are not limited to, the Sessile method or the Captive Bubble method.

EXAMPLE 1

Contact Angle Measurements for Control Lenses: No Pre-Soaking

The contact angles for pHEMA-MAA lenses (Acuvue2®) and silicone hydrogel lenses (Acuvue Advance®, $O_2$ Optix® and Pure Vision®), none having been exposed to a pre-soak treatment in a surfactant solution, were measured as described in this Example 1. The contact angle results are reported in Table 1 below, will hereinafter be referred to as the "Control Lens Results."

Four different brands of contact lenses (one pHEMA-MAA lens type: Acuvue 2®; and three silicon hydrogel lens types: Acuvue Advance®, $O_2$Optix® and Pure Vision®) were soaked in Unisol® saline solution overnight to remove residual packing solution contaminants, prior to measuring the contact angles. The contact angle of each lens was then measured according to the Sessile drop method, as described below, at room temperature, i.e, 23° C.±0.5. The results are presented in Table 1, below.

Sessile Drop Method

A video based contact angle measuring system (OCA 20) from Future Digital Scientific employing SCA20 software (Version 2.1.5 build 16) was used. An accelerated approach was developed to evaluate the lens surface wettability over a specific time period. The pHEMA-MAA lenses were subjected to sequential wetting and air exposure cycles to simulate the clinical contact lens wetting and drying conditions that occur during the normal blinking process. One "cycle" means that a lens was soaked in saline solution for 5 minutes, followed by an exposure of the lens to air for 1.5 minutes. The contact angles of a water droplet on the pHEMA-MAA surface were measured within 10 seconds following each cycle. In all measurements, the left and right contact angles were determined and the mean of these contact angles was used. For each drop image, three independent fitting measurements were performed to provide three mean contact angles of the same drop image. The average of these three contact angles was determined and the precision was within ±3°. This procedure was repeated on three new pHEMA-MAA lenses to confirm the reproducibility of the method.

TABLE 1

| | Contact Angle Measurement for Various Lens Types (°) | | | |
|---|---|---|---|---|
| Cycle Number | Acuvue 2 ® | Acuvue Advance ® | $O_2$Optix ® | Pure Vision ® |
| 0 | 69 | 103 | 30 | 90 |
| 1 | 83 | 105 | 32 | 94 |
| 2 | 102 | 109 | 40 | 95 |
| 3 | 95 | 107 | 44 | 95 |
| 4 | 101 | 108 | 51 | 96 |
| 5 | 101 | 103 | 50 | 95 |
| 6 | 94 | 102 | 56 | 93 |
| 7 | 109 | 106 | 60 | 96 |
| 8 | 112 | 106 | 57 | 93 |

The above data demonstrate that the contact angle for all lens types increases as the number of cycles increases. The high contact angles observed for Acuvue 2®, Acuvue Advance® and Pure Vision® indicate that the surfaces of these lenses were hydrophobic and displayed poor wetting properties towards water.

EXAMPLE 2

Amount of Tetronic® 1304 and $(EO)_{45}$—$(BO)_{14}$ Uptake by pHEMA-MAA (Acuvue2®) and Silicone Hydrogel (Acuvue Advance®) Lenses after a Pre-Soak in Surfactant Solutions A, B and C All contact lenses were soaked in Unisol® saline solution overnight to remove residual packing solution contaminants. Surfactant solutions A, B and C were prepared by dissolving each of the formulation components, as shown in Table 2 below, in water. Into a clean glass vial, one lens of each type (i.e., one Acuvue 2® one Acuvue Advance®) was taken directly from the pack and pre-soaked in 10 ml of each surfactant solution for 24 hours. The lenses were then removed from the solutions and blotted dry. The lenses were then rinsed by immersion in Unisol® saline solution (10 mL), removed from the vials, patted dry and stored in a glass vial. The uptake concentration was then measured using the dye method as reported in Ketelson et al., Colloids and Surfaces Biointerfaces, vol. 40, pages 1-9 (2005). The uptake concentration of Tetronic® 1304 in Acuvue Advance® silicone hydrogel lenses, treated with formulation A was below detection limit (b.d.l.). The other results are shown in Table 2 below:

TABLE 2

Contact Lens Uptake of Tetronic® 1304 and $(EO)_{45}$-$(BO)_{14}$

| Formulation Component | Surfactant Solution (% wt/% vol) | | |
|---|---|---|---|
| | A | B | C |
| Polyquad® | 0.0002 | 0.00025 | 0.00025 |
| $(EO)_{45}$-$(BO)_{14}$ | — | 0.04 | 0.09 |
| Tetronic® 1304 | 0.1 | — | — |
| Sorbitol | 1.0 | 1.0 | 1.0 |
| EDTA | 0.05 | 0.05 | 0.05 |
| Sodium Chloride | 0.3 | 0.3 | 0.3 |
| Sodium Borate | 0.6 | 0.6 | 0.6 |
| Propylene Glycol | 1.0 | 1.0 | 1.0 |
| Purified Water | QS | QS | QS |
| pH | 8.0 | 8.0 | 8.0 |

| | Uptake Concentration of Surfactants (μg/Lens) | | |
|---|---|---|---|
| Lens Type | A | B | C |
| Acuvue 2® | 6.3 | 6.0 | 10.2 |
| Acuvue Advance® | b.d.l | 18.6 | 25.9 |

The above data demonstrate that significant levels of Tetronic® 1304 and $(EO)_{45}$—$(BO)_{14}$ were measured in both Acuvue 2® and Acuvue Advance® lenses. In particular, $(EO)_{45}$—$(BO)_{14}$ was found to have significant uptake for the Acuvue Advance® (silicone hydrogel) lens, as demonstrated by the results obtained with formulations B and C, whereas there was no detectable uptake of Tetronic® 1304 by the Acuvue Advance® silicone hydrogel lenses treated with formulation A.

EXAMPLE 3

Contact Angle Measurements for Acuvue 2® (pHEMA-MAA) and Various Silicone Hydrogel Lenses after a Pre-Soak in 0.1% $(EO)_{45}$—$(BO)_{14}$ Solution (in Unisol®)

All contact lenses were soaked in Unisol® saline solution overnight to remove residual packing solution contaminants. The lenses were then pre-soaked for 24 hours in a 0.1% $(EO)_{45}$—$(BO)_{14}$ solution (in Unisol®). The contact angle of each lens was then measured according to the Sessile drop method, as described above in Example 1, at room temperature, i.e, 23° C.±0.5.

TABLE 3

| | Contact Angle Measurement for Various Lens Types (°) | | | |
|---|---|---|---|---|
| Cycle Number | Acuvue 2® | Acuvue Advance® | O₂Optix® | Pure Vision® |
| 0 | 0 | 0 | 0 | 0 |
| 1 | 0 | 0 | 0 | 0 |
| 2 | 0 | 0 | 0 | 0 |
| 3 | 0 | 0 | 34 | 0 |
| 4 | 12 | 0 | 40 | 0 |

TABLE 3-continued

| | Contact Angle Measurement for Various Lens Types (°) | | | |
|---|---|---|---|---|
| Cycle Number | Acuvue 2® | Acuvue Advance® | O₂Optix® | Pure Vision® |
| 5 | 50 | 0 | 44 | 0 |
| 6 | 40 | 0 | 45 | 0 |
| 7 | 33 | 0 | 46 | 0 |
| 8 | 75 | 0 | 39 | 0 |

The above data demonstrate that the contact angle for all lens types decreases relative to the control lenses (see Example 1 above). Pre-soaking the lenses in a 0.1% $(EO)_{45}$—$(BO)_{14}$ solution in Unisol® saline reduced the contact angles, indicating that the surfaces of all lens types were more wettable towards water compared to their original surface properties.

EXAMPLE 4

Contact Angle Measurements for Acuvue 2® (pHEMA-MAA) and Various Silicone Hydrogel Lenses after a Pre-Soak in a Binary Surfactant Solution Containing 0.1% $(EO)_{45}$—$(BO)_{14}$ and 0.1% Tetronic® 1304 (in Unisol®)

All contact lenses were soaked in Unisol® saline solution overnight, to remove residual packing solution contaminants. The lenses were then presoaked for 24 hours in a binary surfactant solution containing 0.1% $(EO)_{45}$—$(BO)_{14}$ and 0.1% Tetronic® 1304 (in Unisol® saline). The contact angle of each lens was then measured according to the Sessile drop method, as described above in Example 1, at room temperature, i.e, 23° C.±0.5.

TABLE 4

| | Contact Angle Measurement for Various Lens Types (°) | | | |
|---|---|---|---|---|
| Cycle Number | Acuvue 2® | Acuvue Advance® | O₂Optix® | Pure Vision® |
| 0 | 0 | 0 | 0 | 0 |
| 1 | 0 | 0 | 0 | 0 |
| 2 | 0 | 0 | 16 | 0 |
| 3 | 0 | 0 | 14 | 0 |
| 4 | 0 | 0 | 26 | 0 |
| 5 | 0 | 0 | 30 | 0 |
| 6 | 0 | 0 | 0 | 0 |
| 7 | 0 | 0 | 0 | 0 |
| 8 | 0 | 0 | 14 | 0 |

The above data demonstrate that the contact angles for all lens types decreased relative to the control lenses (see Example 1). Pre-soaking the lenses in the binary solution containing both $(EO)_{45}$—$(BO)_{14}$ and 0.1% Tetronic® 1304 led to a significant reduction in the contact angles across all lens types, thereby improving wettability of the lenses.

EXAMPLE 5

Amount of Tetronic® 1304, Tetronic® 1107, $(EO)_{45}(BO)_{14}$ and $(EO)_{20}(BO)_5$ Uptake by pHEMA-MAA (Acuvue 2®) and Silicone Hydrogel (Acuvue Advance®, O₂ Optix® and Pure Vision®) Lenses after a Pre-Soak in Surfactant Solutions A, B, C and D Three lenses of each type were soaked in Unisol® saline solution overnight to remove residual packing solution contaminants. Surfactant solutions A, B, C and D were prepared by dissolving each of the formulation components, as shown in Table 5 below, in Unisol® saline solution. Into a clean glass vial, three lenses of each type (i.e., Acuvue 2®, Acuvue Advance®, O₂ Optix® and Pure Vision®) were taken directly from the pack and pre-soaked in 10 mL of each surfactant solution. The lenses were then removed from the solutions and blotted dry. The lenses were then rinsed by immersion in Unisol® saline solution (10 mL), removed from the vials, patted dry and stored in a glass vial (3 lenses per vial). The uptake concentration was then measured using the dye method identified in Example 2 above. The uptake concentration was reported as the as the average of 3 lenses per lens material type. The uptake results (Table 5) showed significant uptake enhancements using $(EO)_{45}$—$(BO)_{14}$ for the silicone hydrogel lenses compared to the Tetronic® block copolymers bearing poly(oxypropylene) as the hydrophobe block.

TABLE 5

| Surfactant | Surfactant Solution (% wt/% vol) | | | |
|---|---|---|---|---|
| | A | B | C | D |
| Tetronic ® 1304 | 0.1 | — | — | — |
| Tetronic ® 1107 | — | 0.1 | — | — |
| $(EO)_{45}$-$(BO)_{14}$ | — | — | 0.1 | — |
| $(EO)_{20}(BO)_5$ | — | — | — | 0.1 |
| Unisol ® | QS | QS | QS | QS |

| | Uptake Concentration of Surfactants (μg/Lens) | | | |
|---|---|---|---|---|
| Lens Type | A | B | C | D |
| Acuvue Advance | 9 | 16 | 36 | 9 |
| O₂ Optix | 3 | 2 | 2 | 3 |
| Pure Vision | 2 | 3 | 16 | 8 |
| Acuvue 2 | 10 | 5 | 6 | 11 |

The above data demonstrate significant uptake enhancements upon using $(EO)_{45}$—$(BO)_{14}$ for the most hydrophobic silicone hydrogel lenses (Pure Vision® and Acuvue Advance®). These results demonstrate the ability of PEO-PBO block copolymers to interact strongly with hydrophobic surfaces. The improved wettability of the silicone hydrogel lenses (see Examples 3 and 4) is believed to reflect the presence of the PEO-PBO block copolymer at the surface of the lens materials.

EXAMPLE 6

Contact Angle Measurements for Acuvue 2® (pHEMA-MAA) and Acuvue® Advance® after a Pre-Soak in a Binary Surfactant Solution Containing 0.1% $(EO)_{45}$—$(BO)_{10}$ and 0.05% Tetronic® 1304 (in Unisol®)

All contact lenses were soaked in Unisol® saline solution overnight, to remove residual packing solution contaminants. The lenses were then presoaked for 24 hours in surfactant solutions containing either: 0.05% Tetronic® 1304 (Formulation A); or 0.1% $(EO)_{45}$—$(BO)_{10}$ and 0.05% Tetronic® 1304 (Formulation B). The contact angle of each lens was then measured according to the Sessile drop method, as described above in Example 1, at room temperature, i.e, 23° C.±0.5.

TABLE 6

| Formulation Component | Surfactant Solution (% wt/% vol) | |
|---|---|---|
| | A | B |
| Polyquad ® | 0.001 | 0.001 |
| ALDOX ® | 0.0005 | 0.0005 |
| $(EO)_{45}$-$(BO)_{10}$ | — | 0.1 |
| Tetronic ® 1304 | 0.05 | 0.05 |
| Sorbitol | 1.2 | 1.2 |
| EDTA | 0.05 | 0.05 |
| Boric Acid | 0.6 | 0.6 |
| Sodium Citrate | 0.65 | 0.65 |
| Sodium Chloride | 0.1 | 0.1 |
| EDTA | 0.05 | 0.05 |
| AMP-95 | 0.45 | 0.45 |
| Purified Water | QS | QS |
| pH | 7.8 | 7.8 |

| | Contact Angle Measurement for Various Lens Types (°) | | | |
|---|---|---|---|---|
| | Acuvue 2 ® | | Acuvue Advance ® | |
| Cycle Number | Formulation A | Formulation B | Formulation A | Formulation B |
| 0 | 0 | 0 | 0 | 0 |
| 1 | 0 | 0 | 0 | 0 |
| 2 | 0 | 0 | 76 | 0 |
| 3 | 0 | 0 | 76 | 0 |
| 4 | 0 | 0 | 76 | 0 |
| 5 | 0 | 0 | 47 | 0 |
| 6 | 0 | 0 | 93 | 0 |
| 7 | 0 | 0 | 82 | 0 |
| 8 | 0 | 0 | 88 | 0 |

The above data demonstrate that the contact angles for the Acuvue 2 lens type decreased for both Formulation A and B relative to control lenses. However, pre-soaking the Acuvue Advance lenses in the solution containing 0.05% Tetronic® 1304 (Formulation A) showed relatively elevated contact angles. Comparatively, soaking the Acuvue Advance lenses in the binary solution (Formulation B) containing both 0.1% $(EO)_{45}$—$(BO)_{10}$ and 0.05% Tetronic® 1304 led to a significant reduction in the contact angle, thereby improving wettability of the lenses.

We claim:

1. A sterile ophthalmic composition comprising 0.001 w/v % to 1% w/v of at least one poly(oxyethylene)-poly(oxybutylene) block copolymer having a molecular weight in the range of 500 to 100,000 Daltons, an ophthalmically acceptable antimicrobial agent in an amount effective to disinfect a contact lens, and an ophthalmically acceptable vehicle therefor, said composition being a solution suitable for the wetting, cleaning and/or disinfecting of contact lenses and having an osmolality of 200 to 400 milliosmoles/kilogram.

2. A composition according to claim 1, wherein the poly (oxyethylene)-poly(oxybutylene) block copolymer is of the formula $(EO)_m(BO)_n$, wherein EO is oxyethylene and BO is oxybutylene, and wherein m is an integer having an average value of 10 to 1000 and n is an integer having an average value of 5 to 1000.

3. A composition according to claim 2, wherein m is greater than n.

4. A composition according to claim 3, wherein the ratio of m to n is in the range of about 2:1 to about 10:1.

5. A composition according to claim 4, wherein the ratio of m to n is in the range of about 3:1 to about 6:1.

6. A composition according to claim 5, wherein the average value of m is 45 and the average value of n is 10.

7. A composition according to claim 1, wherein the poly(oxyethylene)-poly(oxybutylene) block copolymer has a molecular weight in the range of 1,000 to 50,000 Daltons.

8. A composition according to claim 7, wherein the poly(oxyethylene)-poly(oxybutylene) block copolymer has a molecular weight in the range of 2,000 to 10,000 Daltons.

9. A composition according claim 1, wherein the poly(oxyethylene)-poly(oxybutylene) block copolymer is of the formula

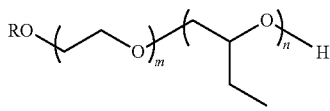

wherein R is selected from the group consisting of hydrogen, methyl, ethyl, propyl and butyl;
m is an integer having an average value of 10 to 1000; and
n is an integer having an average value of 5 to 1000.

10. A composition according to claim 9, wherein R is methyl; m has an average value of 45; and n has an average value of 10.

11. A composition according to claim 1, further comprising an effective amount of a poly(oxyethylene)-poly(oxypropylene) block copolymer.

12. A composition according to claim 11, wherein the poly(oxyethylene)-poly(oxypropylene) block copolymer comprises poloxamine 1304.

13. A composition according to claim 1, wherein said antimicrobial agent comprises polyquaternium-1.

14. A composition according to any one of claims 1-12 and 13, comprising 0.05 w/v % to 0.5 w/v % poly(oxyethylene)-poly(oxybutylene) block copolymer.

15. A composition according to any one of claims 1-12 and 13, comprising 0.1% w/v % to 0.2 w/v % poly(oxyethylene)-poly(oxybutylene) block copolymer.

16. A composition according to any one of claims 1-12 and 13, comprising 0.1 w/v % poly(oxyethylene)-poly(oxybutylene) block copolymer.

17. A method of treating a contact lens to modify the surface characteristics of the lens or clean the lens, which comprises applying an effective amount of a composition according to any one of claims 1-12 and 13 to the lens.

* * * * *